United States Patent [19]
Ciezki et al.

[11] Patent Number: 6,033,357
[45] Date of Patent: *Mar. 7, 2000

[54] INTRAVASCULAR RADIATION DELIVERY DEVICE

[75] Inventors: Jay P. Ciezki, Shaker Heights, Ohio; Eugene J. Jung, Jr., San Diego, Calif.

[73] Assignees: Navius Corporation, San Diego, Calif.; The Cleveland Clinic Foundation, Cleveland, Ohio

[*] Notice: This patent issued on a continued prosecution application filed under 37 CFR 1.53(d), and is subject to the twenty year patent term provisions of 35 U.S.C. 154(a)(2).

[21] Appl. No.: 08/827,489

[22] Filed: Mar. 28, 1997

[51] Int. Cl.$^7$ .................................................. A61M 36/12
[52] U.S. Cl. .................................................. 600/3
[58] Field of Search ........................... 600/1–9; 604/282, 604/280, 264

[56] References Cited

U.S. PATENT DOCUMENTS

| | | |
|---|---|---|
| 4,799,479 | 1/1989 | Spears . |
| 5,019,075 | 5/1991 | Spears et al. . |
| 5,053,033 | 10/1991 | Clarke . |
| 5,199,939 | 4/1993 | Dake et al. . |
| 5,213,561 | 5/1993 | Weinstein et al. . |
| 5,283,257 | 2/1994 | Gregory et al. . |
| 5,302,168 | 4/1994 | Hess . |
| 5,344,402 | 9/1994 | Crocker . |
| 5,345,945 | 9/1994 | Hodgson et al. . |
| 5,354,257 | 10/1994 | Roubin et al. . |
| 5,358,959 | 10/1994 | Halperin et al. . |
| 5,503,613 | 4/1996 | Weinberger ................................. 600/3 |
| 5,562,594 | 10/1996 | Weeks . |
| 5,569,220 | 10/1996 | Webster, Jr. ............................. 604/282 |
| 5,643,171 | 7/1997 | Bradshaw et al. .......................... 600/1 |
| 5,683,345 | 11/1997 | Waksman et al. . |

FOREIGN PATENT DOCUMENTS

| | | | |
|---|---|---|---|
| 9102312 | 8/1992 | Germany ................................. 600/3 |
| 96/10436 | 4/1996 | WIPO ........................................ 600/3 |

OTHER PUBLICATIONS

Frank M. Waterman, Ph.D & David E. Holcomb, Ph.D, Dose Distributions Produced by a Shielded Vaginal Cylinder Using a High–Activity Iridium–192 Source, Philadelphia, Pennsylvania. There is evidence that this document was available at least as early as Jan., 1995.

Nucletron® Corporation, Applicators catalog, Columbia, Maryland. The Applicants are unsure about the date of this publication. However, the number "92" is listed on the back cover, in the bottom right hand corner. Therefore, the catalog may have been published in 1992.

Mayberg et al., "Radiation Inhibition of Intimal Hyperplasia after Arterial Injury", *Radiation Research*, No. 142, pp. 212–220 (1995).

Popowski, et al, "High Dose Rate Brachytherapy for Prevention of Restenosis after Percutaneous Transluminal Coronary Angioplasty: Preliminary Dosimetric Tests of a New Source Presentation", Int. J. Radiation Oncolony Biol. Phys., vol. 33, No. 1 pp. 211–215 (1995).

(List continued on next page.)

*Primary Examiner*—John P. Lacyk
*Assistant Examiner*—Samuel Gilbert
*Attorney, Agent, or Firm*—Nydegger & Associates

[57] ABSTRACT

A delivery device and method for delivering a dosage of radiation from a radiation source to a treatment site of a vessel is provided herein. The delivery device includes a catheter and a delivery area. The catheter is suitable for being inserted into a vessel lumen of the vessel and includes a delivery lumen for receiving the radiation source. The delivery area also receives the radiation source. The delivery area includes an attenuator section for attenuating a portion of the radiation emitting from the radioactive area so that the delivery area emits an eccentric radiation profile. The delivery device can also include a catheter supporter which inhibits rotational deformation in the catheter between a catheter distal end and a catheter proximal end. This allows the delivery area to be precisely rotated to properly position the attenuator section within the vessel lumen.

20 Claims, 6 Drawing Sheets

OTHER PUBLICATIONS

Shimotakahara, et al, "Gamma Irradiation Inhibits Neointimal Hyperplasia in Rats After Arterial Injury", Department of Otolaryngology Head and neck Surgery (S.S.) and Neurological Surgery (M.R.M.) University of Washington, Seattle VA Medical Center, Seattle, Wash., pp. 424–428, accepted Sep. 13, 1993 *Stroke*, vol. 25, No. 2, Feb. 1994.

Waksman et al., "Intracoronary Low–Dose B–Irradiation Inhibits Neointima Formation After Coronary Artery Balloon Injury in the Swine Restenoisi Model", From Andreas Gruentzig Cardiovascular center Division of cardiology, Department of Medicine (R.W., K.A.R., G.D.C., S.B.K.); Department of Radiation Oncology (I.R.C.); Department of Pathology, Emory University School of Medicine (M.B.G.); Health Physics program, Georgia Institute of Technology (C.W.); and Novoste Corporation (R.A.H.), Atlanta, Ga., pp. 3025–3031, accepted Jun. 13, 1995.

Wiedermann, et al, "Effects of High–Dose Intracoronary Irradiation on Vasomotor Function and Smooth Muscle Histopathology", *Intracoronary Irradiation and Vasomotion*, The American Physiological Society, pp. H125–H132, (1994) *Circulation*, Vo. 92, No. 10, Nov. 15, 1995.

Weidermann, et al, "Intracoronary irradiation markedly Reduces Restenosis after Baloon Angioplasty in a Porcine Model", Departments of Medicine and Radiation Oncology, and Section of Presbyterian Medical Center and Columbia University, New York, New York, accepted Dec. 22, 1993. *JACC*, vol. 23, No. 6, May 1994, pp. 1491–1498.

Weidermann, et al, "Intracoronary Irradiation markedly Reduces Neointimal Proliferation After Balloon Angioplasty in Swine: Persisent Benefit at 6–Month Follow–Up" *JACC*, vol. 25, No. 6, May 1995; pp. 1451–1456.

Popowski, et al, "Endovascular B–Irradiation after Percutaneous Transluminal Coronary Balloon Angioplasty", *Int. J. Radiation Oncology Bio. Phys.*, vol. 36, No. 4, pp. 841–845, (1996).

Schopohl, et al. "Ir Endovascular Brachytherapy for avoidance of Intimal Hyperplasia after percutaneous Transluminal Angioplasty and Stent Implantation in Peripheral Vessels: 6 Years of Experience" *Int. J. Radiation Oncology Bio. Phys.*, vol 36, No. 4, pp. 835–840, (1996)., Marcial–Rojas–Castro, San Juan Puerto Rico, "Irradiation Injury to Elastic Arteries in the Course of Treatment for Neoplastic Disease," From the Department of Pathology of the University of Puerto Rico School of Medicine and the Dr. I. Gonzáalez Martinez Oncologic Hospital.

Sinzinger et al. "Enhanced Mitotic Activity Induced by Irradiation is Abolished by PGI2 Pretreatment," *Prostaglandins*, Jan., 1991, vol. 41, No. 1., pp. 57–65.

Martin, et al., "Elastin Synthesis and Accumulation in Irradiated Smooth Muscle Cell Cultures," *Connective Tissue Research*, 1992, vol. 28, pp. 181–189.

Eldor, et al., "Perturbation of Endothelial Functions by Ionizing Irradiation: Effects on Prostaglandins, Chemoattractants and Mitogens," Seminars in Thrombosis and Hemostasis, vol. 15, No. 2, pp. 215–225, 1989.

Applefeld, et al., "Cardiac Disease After Radiation Therapy for Hodgkin's Disease: Analysis of 48 Patient", The American Journal of Cardiology, pp. 1679–1681, vol. 51, Jun., 1983.

Hicks, George L. M.D., "Coronary Artery Operation in Radiation–Associated Atherosclerosis: Long–Term Follow–up," *Ann Thorac, Surg,*; 53, pp. 670–674, (1992).

Fajardo, et al, "Morphology of Radiation–Induced Heart Disease", *Arch Path*, vol. 86, Nov. 1968, pp. 512–519.

Wilcox, et al, "The Role of the Adventitia in the Arterial Response to Angioplasty: The Effect of Intravascular Radiation", Int. J. Radiation Oncology Biol. Phys. vol. 36, No. 4, pp. 789–796, 1996.

Sinzinger, et al., "Morphologische und Zellkinetische Untersuchungen an der Arterienward nach Röntgenbestrahlung. I Ergebnisse bei 3000rad. Herdbestrahlungdosis am Kaninchen", *Acta Morphio. Nerf.–Scand* 14 (1976), pp. 201–214, Apr. 27, 1975.

*Fig. 8*

INTRAVASCULAR RADIATION DELIVERY DEVICE

FIELD OF THE INVENTION

The present invention relates generally to a device and method for treating a blockage or stenosis in a vessel of a patient. More specifically, the present invention relates to a device and method for precisely delivering a dosage of radiation to a vessel to inhibit re-stenosis.

BACKGROUND

It is well known that many medical complications are caused by a partial or total blockage or stenosis of a blood vessel in a patient. Depending on the location of the stenosis, the patient can experience cardiac arrest, stroke or necrosis of tissues or organs. Commonly, the stenosis is caused by the build-up of artherosclerotic plaque in the intima of the vessel. The plaque typically builds up irregularly in the vessel. As a result of the irregular build-up of plaque, the lumen of the vessel, in most blocked vessels, is not centrally located relative to the external elastic lamina.

Several procedures have been developed to treat stenoses, including angioplasty, stenting, and atherectomy. However, none of these procedures are entirely successful in inhibiting or preventing the re-stenosis of a vessel after the procedure is completed.

Recent studies have demonstrated that radiation may inhibit or prevent re-stenosis in the vessel by inhibiting or preventing the growth of fibrotic cells in the vessel wall, commonly referred to as neointima. The precise target for the radiation in the vessel is currently not known. However, it is believed that the adventitia may be a key source of growth of the neointima. Therefore, it is theorized that the entire vessel, including the adventitia should be treated with radiation.

At least one delivery device has been used for performing intravascular radiation treatment on a treatment site of the vessel. This delivery device utilizes a catheter to position a radiation source in the vessel lumen, adjacent the treatment site. The radiation source is positioned in the vessel lumen and is allowed to emit radiation until the proposed dosage is released. With this delivery device, the tissue closest to the radiation source receives a larger radiation dosage than the tissue farthest from the radiation source. Subsequently, the radiation source is removed from the vessel lumen.

However, the results obtained using this type of delivery device are not entirely satisfactory. Specifically, because the growth of the plaque inside the vessel is irregular and/or the vessel is curved, the radioactive source is not centered in the vessel relative to the vessel lamina. Thus, depending upon the dosage prescribed, this can result in undertreating certain portions of the vessel and overtreating certain other portions of the vessel. For example, certain portions of the vessel lamina will receive a larger dosage of radiation than other portions of the vessel lamina.

Undertreating with radiation can result in not inhibiting the neointima and, in some instances, can actually result in stimulating smooth muscle cell proliferation and extracellular matrix production. Overtreating with radiation can, for example, induce necrosis or aneurysm. Therefore, it is important to avoid overtreating and/or undertreating of a treatment site of the vessel.

One attempt to solve this problem involves accurately centering the delivery device in the vessel, relative to the vessel lumen. This can be accomplished using a variety of mechanical devices, such as a centering balloon or an expandable mechanical strut. However, these mechanical devices add excessive mass and bulk to the delivery device. This limits the usefulness of the present delivery device to relatively large vessels, i.e., 3.5 millimeters or larger and increases the risk of occluding blood flow in the vessel. Moreover, there is a risk that the delivery device will not be accurately centered.

In light of the above, it is an object of the present invention to provide a device and method for delivering a precise dose of radiation to a treatment site of a vessel without centering the delivery device. It is another object of the present invention to provide a device and method for delivering a substantially uniform dose of radiation to the vessel lamina and other areas of the vessel. Still another object of the present invention is to provide a device and method which is relatively safe and easy to use. Yet another object of the present invention is to provide a device which is relatively simple and inexpensive to manufacture.

SUMMARY

The present invention is directed to a delivery device which satisfies these objectives. The delivery device is useful for delivering a dose of radiation from a radiation source to a treatment site of a vessel to treat a stenosis in the vessel. The delivery device includes a catheter and a delivery area which insert into the vessel. As provided herein, the delivery area includes an attenuator section which attenuates the intensity of a portion of the radiation emitting from the radiation source when a portion of the radiation source is positioned in the delivery area. In use, the attenuator section partly inhibits the intensity of radiation directed at where the vessel wall is the thinnest. This prevents overtreatment of the vessel.

As used herein, the term "radiation dose profile" refers to and means the cross-sectional pattern of energy being delivered from the delivery area of the delivery device. A more comprehensive definition of radiation dose profile is provided in the description section.

As used herein, the term "vessel wall" refers to and means the structural support of the vessel. For an artery, the vessel wall would include an endothelium, a basement membrane, a vessel intima, an eternal elastic lamina, a vessel media, a vessel external elastic lamina (hereinafter "vessel lamina"), and a vessel adventitia. For a diseased artery, the vessel wall can also include atherosclerotic plaque which infiltrates the vessel intima and causes stenosis of the vessel.

As provided in detail below, since the attenuator section attenuates a portion of the radiation emitting from the radioactive area, the delivery area emits a radiation dose profile which is substantially eccentric. With an eccentric radiation dose profile, more radiation can be directed at where the vessel wall is the thickest, while less radiation can be directed to where the vessel wall is the thinnest. This can be accomplished by rotating the delivery area until the attenuator section is substantially closest to the vessel lamina. Since, the attenuator section attenuates a portion of the radiation directed at where the vessel wall is the thinnest, a substantially uniform dosage of radiation is delivered to the vessel lamina at the treatment area, even though the delivery device is not centered in the vessel relative to the vessel lamina.

The attenuator section includes an attenuator material which at least partly diminishes the intensity of the radiation which emits therefrom. The attenuator material is typically a relatively dense material having a relatively high atomic number. Preferably, the attenuator material is also biocompatible and safe for use in surgery. Materials such as gold, platinum, and tantalum can be used.

Importantly, the shape of the radiation dose profile varies according to the size, shape, and thickness of the attenuator section, as well as the attenuator material utilized. Thus, the attenuator section can be designed so that the radiation dose profile corresponds to the specific size and shape of the vessel wall. As used herein, the phrase "configuration of the attenuator section" shall mean the size, shape, thickness, and material utilized in the attenuator section. Also as used herein the phrase "configuration of the vessel wall" shall mean the size and shape of the vessel wall at the treatment site, including the positioning of the vessel lamina relative to the vessel lumen.

The delivery device also includes a catheter supporter which substantially inhibits rotational deformation in the catheter between a catheter distal end and a catheter proximal end. The catheter supporter allows the delivery area to be precisely rotated by the catheter proximal end to position the filter section adjacent where the vessel wall is the thinnest.

Preferably, the delivery device includes at least one marker positioned proximate the delivery area. The marker is used to indicate the location of the delivery area in the vessel. For example, the marker can be radiopaque and visible with a fluoroscope. This allows the doctor to position the delivery area adjacent the treatment area.

The invention is also a method for delivering radiation from a radiation source to a treatment site of a vessel. The method includes the steps of advancing a catheter into the vessel lumen until a delivery area is positioned substantially adjacent the treatment site, positioning at least a portion of the radiation source proximate the delivery area, and emitting a radiation dose profile from the delivery area which is substantially eccentric.

Further, the method can include the step of rotating the delivery area inside the vessel lumen until the orientation of the attenuator section is substantially closest to the vessel lamina. This step typically includes imaging the vessel to determine when a window section of the delivery area is substantially farthest away from the vessel lamina.

Preferably, the treatment site of the vessel is imaged to determine the configuration of the vessel wall proximate the treatment site. With this information, the configuration of the attenuator section can be chosen.

It is important to recognize that a device in accordance with the present invention utilizes an attenuator section proximate the delivery area so that the delivery area emits a radiation dose profile which is substantially eccentric. Therefore, the delivery device is able to deliver a substantially uniform dose to the vessel lamina, even though the delivery device is not centered relative to the vessel lamina.

BRIEF DESCRIPTION OF THE DRAWINGS

The novel features of this invention, as well as the invention itself, both as to its structure and its operation will be best understood from the accompanying drawings, taken in conjunction with the accompanying description, in which.

DESCRIPTION

Figure 1:
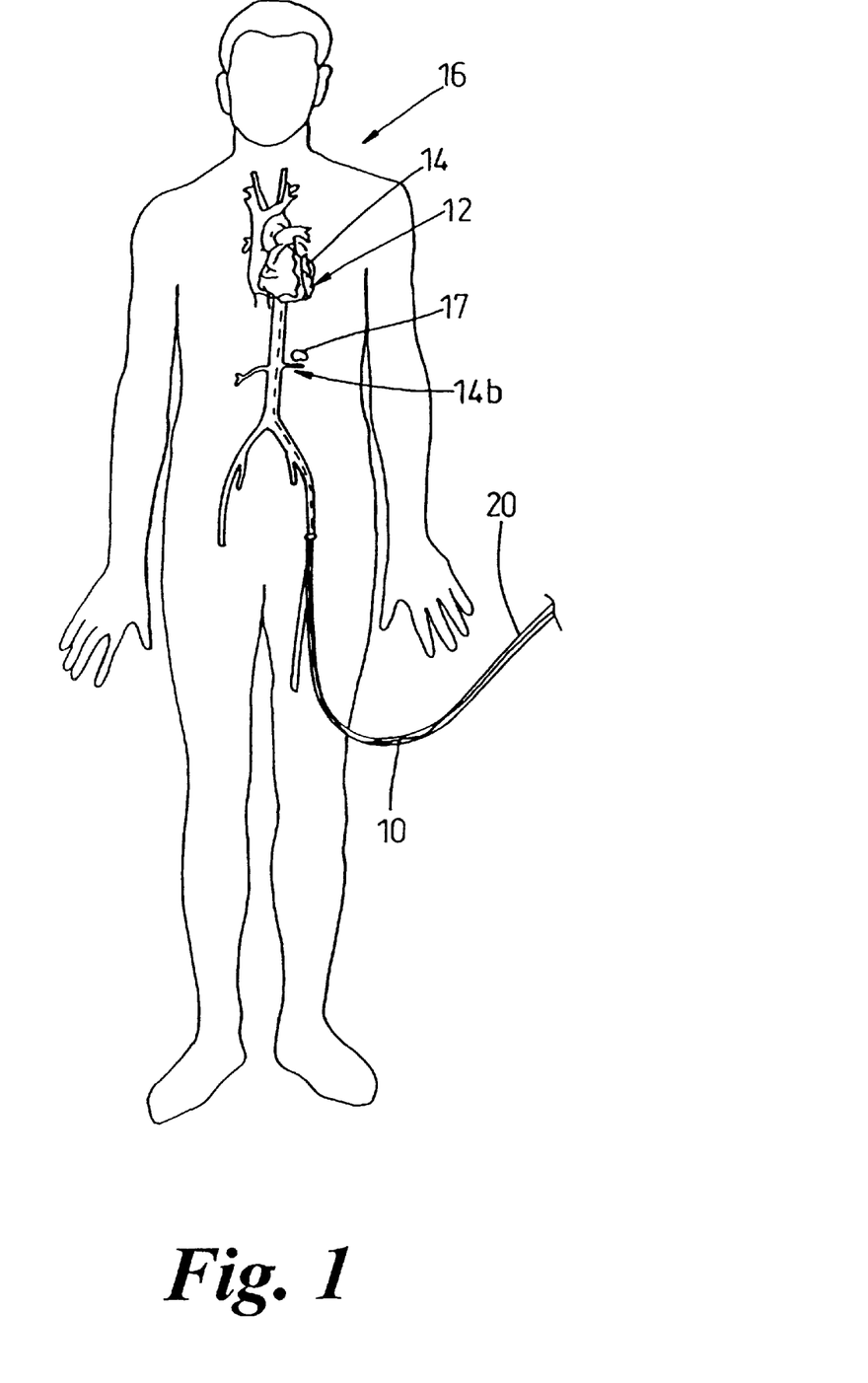
FIG. 1 is a top plan view of a patient with a delivery device having features of the present invention positioned in a vessel of the patient.

Referring initially to FIG. 1, a delivery device 10 for delivering a dosage of radiation to a treatment site 12 of a vessel 14 of a patient 16 is provided herein. The delivery device 10 is useful from treating a vessel wall 18 (shown in FIGS. 3 and 4) of a vessel 14 throughout the vascular system of the patient 16. Although the present invention is particularly useful for inhibiting the re-growth of neointima in coronary arteries, it is anticipated that the present delivery device 10 can be used to treat medical conditions, such as cancer 17, proximate the vessel 14b.

The delivery device 10 may be introduced into the vessel 14 wherever it is convenient. As shown in FIG. 1, the delivery device 10 can be inserted through an external, flexible, tubular shield 20 which partly inhibits the intensity of radiation. The tubular shield 20 diminishes the potential of radiation exposure to the medical staff during use of the present delivery device 10.

A guiding catheter (not shown) is typically used with the present delivery device 10 for the treatment of coronary arteries. A suitable guiding catheter is sold by Medtronic of Minneapolis, Minn.

Figure 2:
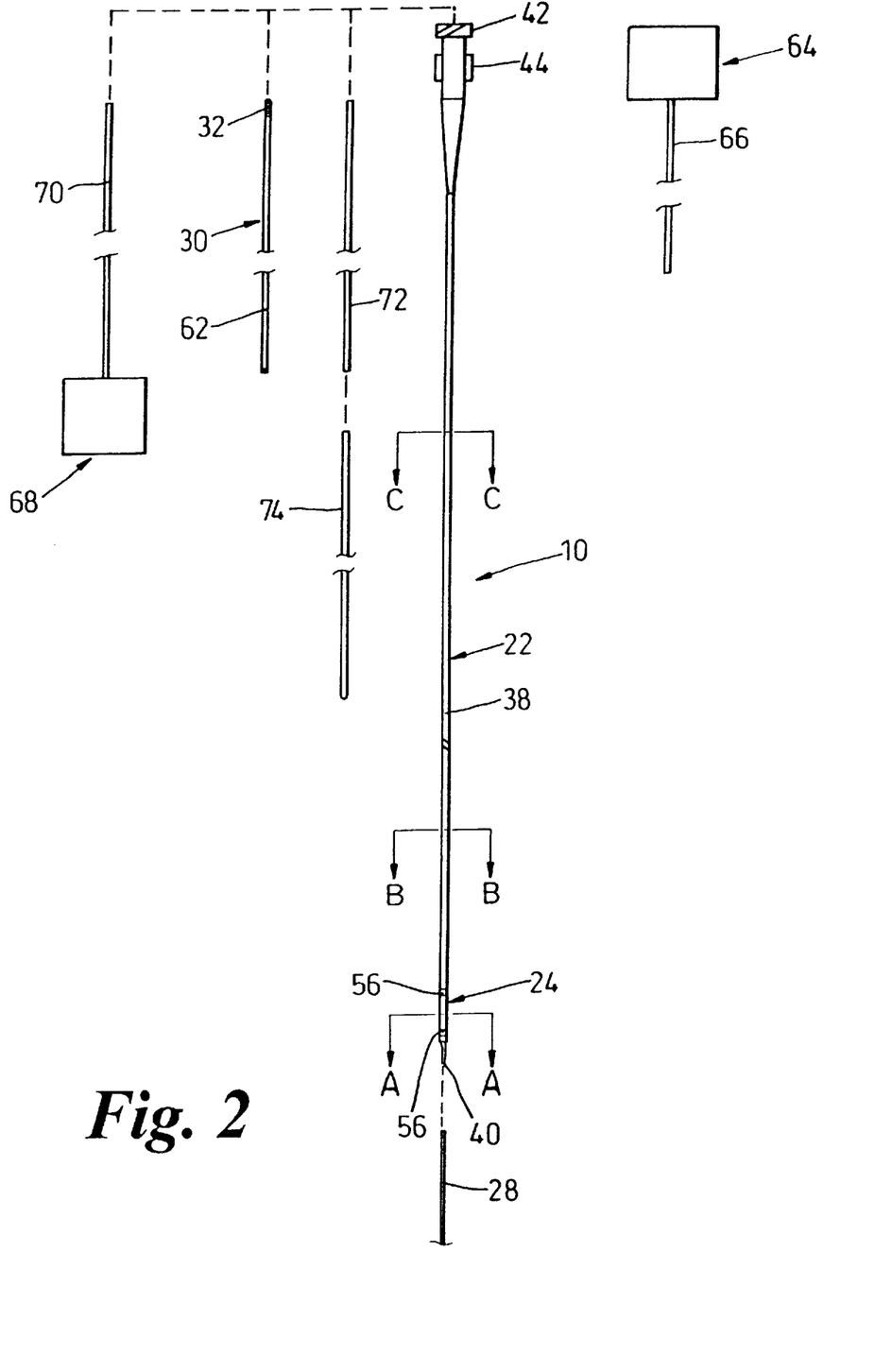
FIG. 2 is an exploded, side plan view of a delivery device having features of the present invention.

The structural details of the delivery device 10 may be more fully appreciated by reference to FIG. 2, where the delivery device 10 includes a catheter 22, a delivery area 24, a catheter supporter 26 (not shown in FIG. 2), a guide wire 28 and a radiation source 30 having a radioactive area 32.

As provided in detail below, the unique design of the delivery area 24 allows the doctor to control the radiation emitting from the delivery area 24 when the radioactive area 32 is positioned in the delivery area 24. Basically, the delivery device 10 is designed to reduce the intensity of radiation proximate where the vessel wall 18 is the thinnest. This allows the doctor to tailor the radiation treatment to suit the configuration of the vessel wall 18 at the treatment site 12. Further, this allows the doctor to deliver a substantially uniform dose of radiation to a vessel lamina 34 to inhibit the growth of neointima in the vessel 14.

It is anticipated that the present delivery device 10 will be used in conjunction with other vascular procedures such as angioplasty, stenting, and/or atherectomy for the treatment of a stenosis 33 in the vessel 14. However, the present device 10 can also be used in lieu of these or other procedures.

Figure 3:
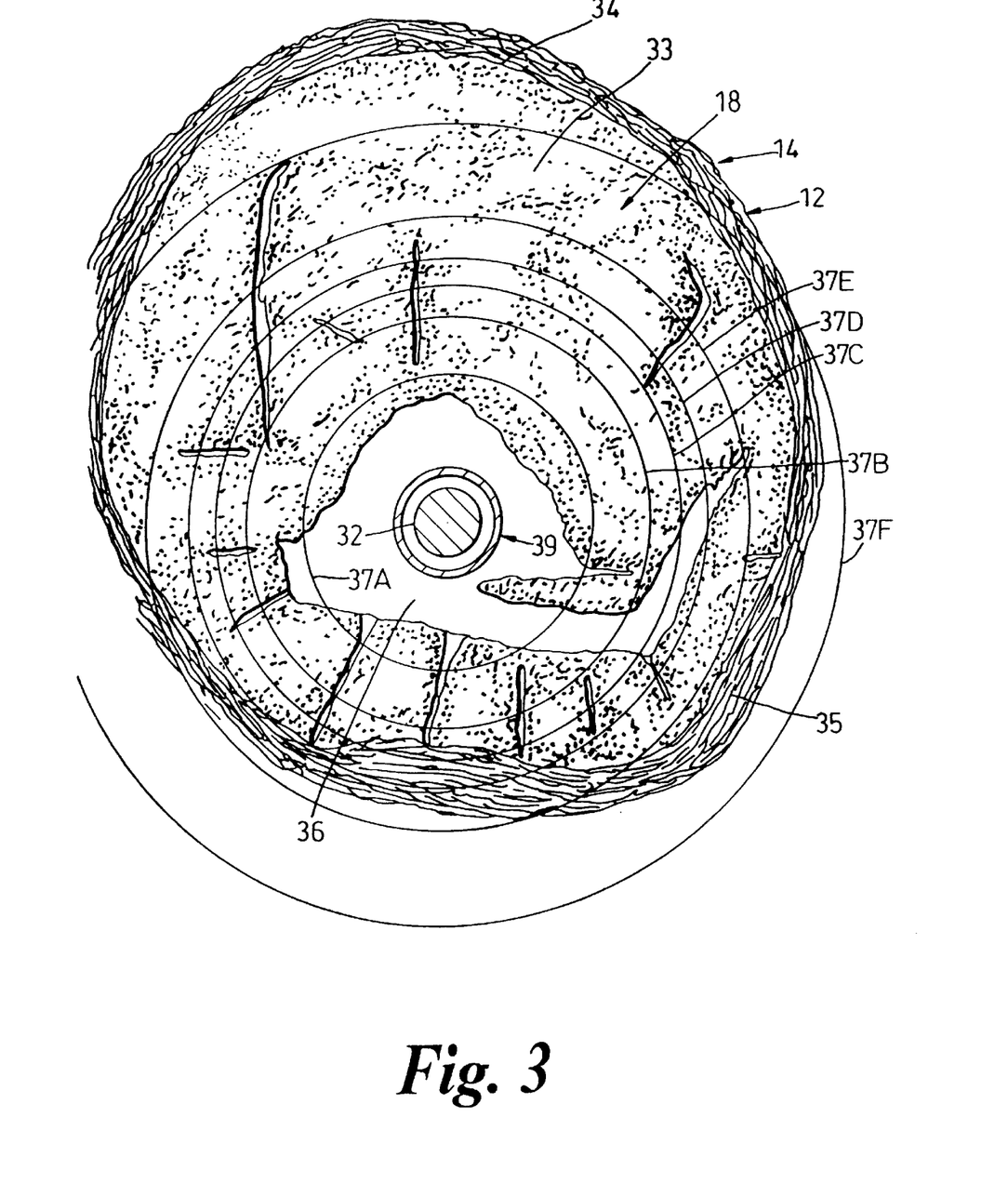
FIG. 3 is a cross-sectional view of a prior art delivery device positioned in a vessel.
Figure 4:
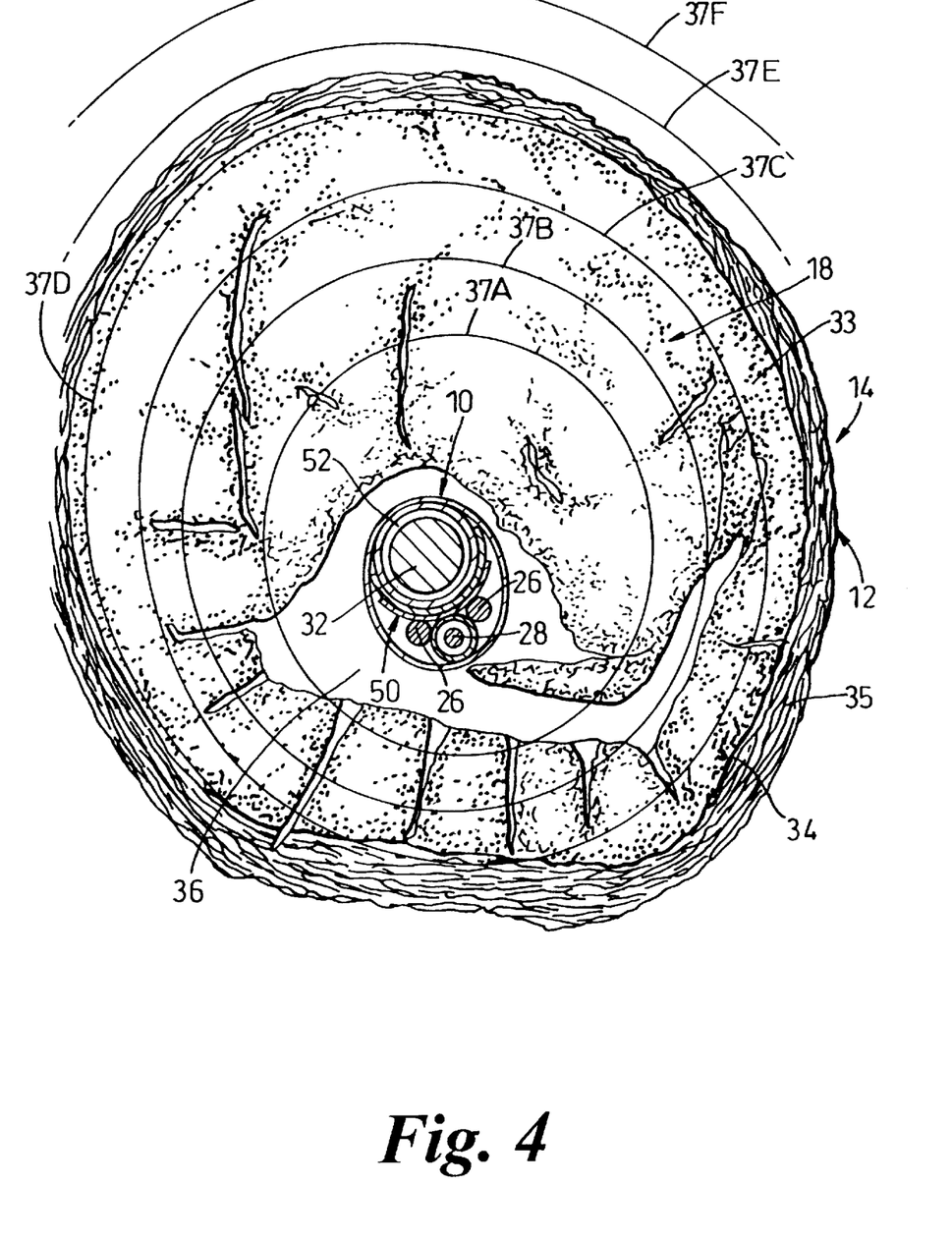
FIG. 4 is a cross-sectional view of a delivery device having features of the present invention positioned in a vessel.
Figure 5:
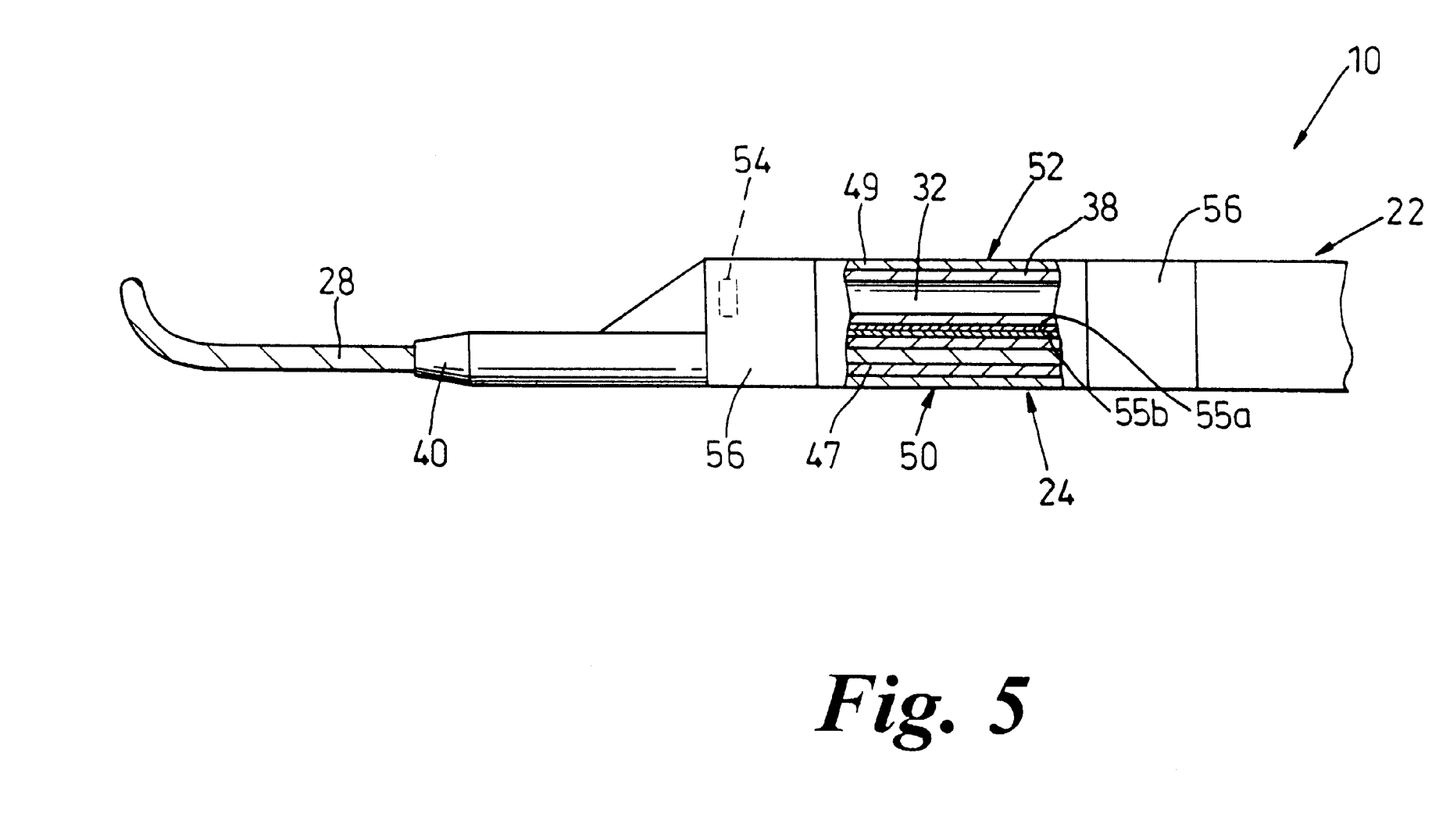
FIG. 5 is an enlarged view, in partial cutaway, of a portion of a delivery device having features of the present invention.

Referring to FIGS. 3 and 4, the vessel wall 18 includes the stenosis 33, a vessel lamina 34, and a vessel adventitia 35. The configuration of the vessel wall 18 defines the size and shape of a vessel lumen 36 and the location of the vessel lumen 36 relative to the vessel lamina 34. In the vessel 14 shown in FIGS. 3 and 4, the vessel wall 18 is irregular and oblong shaped. Thus, the vessel lumen 36 is offset from center and eccentrically positioned relative to the vessel lamina 34. Therefore, the delivery device 10 positioned in the vessel lumen 36, is offset from center and eccentrically positioned relative to the vessel lamina 34. It should be noted that the vessel lumen 36 represented in FIGS. 3 and 4 is the resulting vessel lumen 36 after an angioplasty treatment.

There is considerable debate about the amount of radiation that should be delivered to the vessel 14 to inhibit the growth of neointima. The present delivery device 10 is designed to deliver a dosage of approximately ten (10) to twenty (20) gray of radiation to the vessel lamina 34. However, the present invention is not intended to be limited to these dosages and the dosages provided herein are only exemplary. For example, additional research may determine that dosages of more than or less than ten (10) to twenty (20) gray may be more beneficial to the patient 16.

As used herein, the term radiation dose profile refers to and means the cross-sectional pattern of energy being delivered by the delivery area to the vessel 14. The approximate shape of the radiation dose profile is represented by a plurality of dose curves 37A–F shown in FIGS. 3 and 4. Each dose curve 37A–F represents an approximate area in the vessel 14 which is receiving a substantially uniform dosage of radiation. For example, dose curve 37A can represent the area in the vessel 14 which receives a dosage of approximately thirty (30) gray, dose curve 37B can represent the area in the vessel 14 which receives a dosage of approximately twenty-five (25) gray, dose curve 37C can represent the area of the vessel 14 which receives a dosage of approximately twenty (20) gray, dose curve 37D can represent the area of the vessel 14 which receives a dosage of approximately fifteen (15) gray, dose curve 37E can represent the area in the vessel 14 which receives a dosage of approximately ten (10) gray, and dose curve 37F can represent the area in the vessel 14 which receives a dosage of approximately five (5) gray.

FIGS. 3 shows the dose curves 37A–F from a prior art delivery device 39. For the prior art delivery device 39, the radiation emits equally radially from the radioactive area 32. Thus, the dose curves 37A–F in FIG. 3, are substantially circular and concentric.

From FIG. 3, it can be seen that the vessel lamina 34 does not receive a substantially uniform dosage. In fact, portions of the vessel lamina 34 receive a dosage of approximately twenty (20) gray while other portions of the vessel lamina 34 receive a dosage of less than five (5) gray. Thus, depending upon the actual dosage utilized, portions of the vessel lamina 34 may be undertreated, while other portions of the vessel lamina 34 will be overtreated.

FIG. 4 shows the dose curves 37A–F for a delivery device 10 having features of the present invention. Because of the unique design of the delivery area 24, the dose curves 37A–F in FIG. 4 are not circular. In fact the dose curves 37A–F in FIG. 4 are substantially elliptical or eccentric. As a result thereof, referring to dose curve 37D of FIG. 4, the entire vessel lamina 34 receives a substantially uniform dose of approximately fifteen (15) gray, even though the delivery area 24 is not centered relative to the vessel lamina 34.

The catheter 22 inserts into the vessel 14 and is used to position the radioactive area 32 adjacent the treatment site 12. The catheter 22 includes a tubular outer structure 38 having a catheter distal end 40 and a catheter proximal end 42. The catheter distal end 40 inserts into the vessel lumen 36 and should be as smooth as possible to facilitate insertion into the vessel lumen 36. The catheter proximal end 42 typically remains outside the patient 16. As shown in FIG. 2, the catheter proximal end 42 can include a handle 44 which is used to manipulate and rotate the catheter 22 in the vessel lumen 36.

The outer structure 38 can be made from a variety of materials, such as a block copolymer sold under the trademark Pebax by Elf Atochem North American located in Philadelphia, Pa. or polyethylene. Preferably, the outer structure 38 is coated with a hydrophilic or other lubricious coating to facilitate easy movement of the catheter 22 in the vessel lumen 36.

Referring to FIGS. 5, 6A–C and 7A, the catheter 22 also includes a guide wire lumen 46 for receiving the guide wire 28. The guide wire lumen 46, shown in the Figures, is defined by a guide wire tube 47 having an inner diameter of between about 0.015 to 0.025 inches. The guide wire lumen 46 extends from the catheter proximal end 42 to the catheter distal end 40.

Referring again to FIGS. 5, 6A–C and 7A, the catheter 22 further includes a delivery lumen 48 which is sized and shaped to receive the radiation source 30. Thus, the size and shape of the delivery lumen 48 depends upon the size and shape of the radiation source 30. In the embodiment shown in the Figures, the delivery lumen 48 is defined by a delivery tube 49 having an inner diameter of between about 0.02 to 0.03 inches.

The delivery lumen 48 extends from the catheter proximal end 42 to proximate the catheter distal end 40. The delivery lumen 48 can be sealed proximate the catheter distal end 40 to prevent the radiation source 30 from escaping into the vessel 14 and to prevent direct contact between the blood (not shown) in the vessel 14 and the radiation source 30. Alternately, the delivery lumen 48 can be open proximate the catheter distal end 40.

The delivery tube 49 and the guide wire tube 47 can be made from a number of materials, including a block copolymer or a high density polyethylene.

It is anticipated that the catheter 22 can also include a bypass lumen (not shown) for transporting blood (not shown) in the vessel 14, past the catheter 22, when the catheter 22 is positioned in the vessel 14. Basically, the bypass lumen allows the delivery device 10 to be used in relatively small vessels 14 without interrupting blood intensity in the vessel 14.

The delivery area 24 receives the radioactive area 32 and delivers the radiation to the treatment site 12. As provided herein, the unique design of the delivery area 24 allows the delivery area 24 to emit a radiation dose pattern which is substantially eccentric and elliptical. Thus, a substantially homogenous radiation dose can be delivered to the vessel lamina 34 even though the delivery device 10 is eccentrically positioned relative to the vessel lamina 34.

The length and positioning of the delivery area 24 can be varied to meet the needs of the patient 16. In the embodiment shown in FIG. 5, the delivery area 24 is approximately one half to ten (0.5–10) centimeters long and is positioned proximate the catheter distal end 40.

The delivery area 24 includes an attenuator section 50 and a window section 52 for directing the intensity of radiation emitting from the radioactive area 32. Basically, the attenuator section 50 alters the pattern of radiation emitting from the delivery area 24. This compensates for the irregular shape of the stenosis 18 and for the eccentric positioning of the delivery area 24 relative to the vessel lamina 34.

The attenuator section 50 can be designed to attenuate approximately between about one percent to one hundred percent (1%–100%) of the intensity of the radiation directed toward the attenuator section 50. In contrast, the window section 52 can be designed to attenuate approximately between zero percent to ninety-nine percent (0%–99%) of the intensity of the radiation directed at the window section 52.

In the embodiment described in detail herein, the attenuator section 50 attenuates a relatively significant amount of radiation directed towards the attenuator section 50 while the window section 52 has a relatively negligible or insignificant effect upon the radiation emitting from the delivery area 24.

In this embodiment, the attenuator section 50 attenuates approximately between ten percent to forty percent (10%–40%) of the intensity of radiation directed at the attenuator section 50 while the window section 52 attenuates less than approximately one percent (1%) of the intensity of the radiation directed at the window section 52.

Importantly, it is the difference in the amount of attenuating between the window section 52 and the attenuator section 50 that is significant in determining the radiation dose profile. Conceivably, the attenuator section 50 can attenuate between about one percent to one hundred percent (1%100%) more radiation than the window section 52 to create dose curves 37A–F which are not circular. Typically, for most situations, the attenuator section 50 is designed to attenuate about five percent to ninety percent (5%–90%) and more preferably about ten percent to forty percent (10%–40%) more radiation than the window section 52.

Alternately, to deliver a concentrated dosage of radiation to a specific area, i.e., cancer 17 proximate the vessel 14*b*, the attenuator section 50 can be designed to attenuate between about ninety percent and one hundred percent (90%–100%) more radiation than the window section 52.

In the embodiment shown in the Figures, the attenuator section 50 includes a portion of the delivery tube 49, a first component 55*a* and a second component 55*b*. The first and second components 55*a*, 55*b* include an attenuator material which attenuates the intensity of radiation therethrough. In contrast, the delivery tube 49 is made of a material which has a relatively insignificant effect upon the radiation.

Importantly, the configuration of the attenuator section 50, i.e., the size, shape, thickness, and the attenuator material of the attenuator section 50 can be varied to change the shape of the radiation dose profile to suit the configuration of the vessel wall 18 at the treatment site 12. For example, as the size and thickness of the attenuator section 50 increases, the radiation dose profile becomes increasingly more eccentric. Similarly, as the size and thickness of the attenuator section 50 is decreased, the radiation dose profile becomes increasingly more concentric.

The attenuator material can be made from a number of materials and/or alloys which attenuate radiation. Because of the size limitations of the delivery device 10, the attenuator material is typically a relatively dense material having a relatively high atomic number. Preferably, to minimize the size of the attenuator section 50, the attenuator material has: (i) a density of at least about ten (10) grams per cubic centimeter and more preferably at least about nineteen (19) grams per cubic centimeter; and (ii) an atomic number of at least about twelve (12), and more preferably at least about seventy (70). Further, the attenuator material is preferably bio-compatible so that the attenuator section 50 is compatible with the vessel 14. It is anticipated that gold, platinum, or tantalum can be used as the attenuator material. Alternately, alloys utilizing one or more relatively dense materials can also be used.

In the embodiment shown in the Figures, the first and second components 55*a*, 55*b* are each a piece of thin foil that is between about one (1) to two hundred (200) microns and more preferably between about five (5) to fifty (50) microns thick. Each of the first and second components 55*a*, 55*b* are shaped similar to a semi-circular band. In this embodiment, the first component 55*a* is rolled or wrapped around a portion of the delivery tube 49 while the second component 55*b* is rolled or wrapped around the first component 55*a*. The first component 55*a* can be bonded to the delivery tube 49 and the second component 55*a* can be bonded to the first component 55*a* with a suitable adhesive. Alternately, a retaining tubular conduit (not shown) can be wrapped around and retain the first and second components 55*a*, 55*b* to the delivery tube 49.

In the embodiment shown in FIGS. 4, 6A, 7A, and 8 the first component 55*a* extends approximately two hundred degrees (200°) around the delivery tube 49 while the second component 55*b* extends approximately one hundred and twenty degrees (120°) around the delivery tube 49. It is anticipated that the first component 55*a* can be designed to extend between about two hundred degrees to two hundred and seventy degrees (200°–270°), while the second component 55*b* extends between about one hundred degrees to one hundred and fifty degrees (100°–150°). Further, the positioning of the first and second components 55*a*, 55*b* can be switched.

Alternately, the attenuator section 50 can be implemented in a number of other ways. For example, the attenuator section 50 can be a thin foil of varying thickness, which is rolled completely around a portion of the delivery tube 49. In this embodiment, the foil includes an opening (not shown) which forms the window section 52. Alternately, the attenuator material can be sputtered and then electroplated directly onto the delivery tube 49 or ion beam technology can be used to secure the attenuator material to the delivery tube 49. Further, it is envisioned that the delivery tube 49 could be impregnated with an attenuator material such as barium.

It is anticipated that a plurality of delivery devices 10 will be provided to the hospital and each delivery device 10 will have an attenuator section 50 with a different attenuator configuration. Thus, the doctor will be able to choose the delivery device 10 having the radiation dose profile which most closely matches the configuration of the vessel wall 18.

In the embodiments shown in the Figures, the window section 52 is defined by the portion of the delivery tube 49 which is not covered with the attenuator material. In this embodiment, the delivery tube 49 is made of a material which has a negligible or insignificant effect upon the radiation emitting from the delivery area 24 when compared to the attenuator section 50. In fact, since the attenuator section 50 also includes a portion of the delivery tube 49, the window section 52 basically has no relative effect upon the radiation emitting from the delivery area 24.

Since the window section 52 does not reduce the intensity of the radiation as much as the attenuator section 50, the window section 52 delivers the radiation to a greater depth in the tissue than the attenuator section 50. This enables the delivery device 10 to preferentially deliver more radiation to where the vessel wall 18 is the thickest.

Referring back to FIG. 4, in use, the delivery area 24 is rotated in the vessel lumen 36 until the attenuator section 50 is substantially closest to the vessel lamina 34, while the window section 52 is farthest from the vessel lamina 34. Thus, the attenuator section 50 is proximate where the vessel wall 18 is the thinnest while the window section 52 is proximate where the vessel wall 18 is the thickest.

The catheter 22 can include a radiation blocker 54 (shown in phantom in FIG. 5) positioned proximate the catheter distal end 40 which inhibits radiation from emitting longitudinally from the delivery area 24. The radiation blocker 54, for example, can be a cylindrical disk made from a relatively dense material such a platinum or gold which is positioned in the delivery conduit proximate the catheter distal end 40.

Preferably, the delivery device 10 includes a pair of markers 56 which assist in the positioning of the delivery area 24 proximate the treatment site 12. Referring to the Figures, the markers 56 can each be a band, made from a radiopaque material, which encircles the outer structure 38 of the catheter 22 on each side of the delivery area 24. Since the markers 56 are made of a radiopaque material, such as platinum or gold, the position of the markers 56 is visible using a fluoroscope or x-rays.

The catheter supporter 26 inhibits rotational deformation or twisting of the catheter 22 between the catheter distal end 40 and the catheter proximal end 42. In use, the catheter supporter 26 transmits torque smoothly and predictably between the catheter proximal end 42 and the catheter distal end 40. This allows the delivery area 24 to be precisely rotated with the handle 44 so that the window section 52 is substantially adjacent where the vessel wall 18 is the thickest.

Figures 6A, 6C:
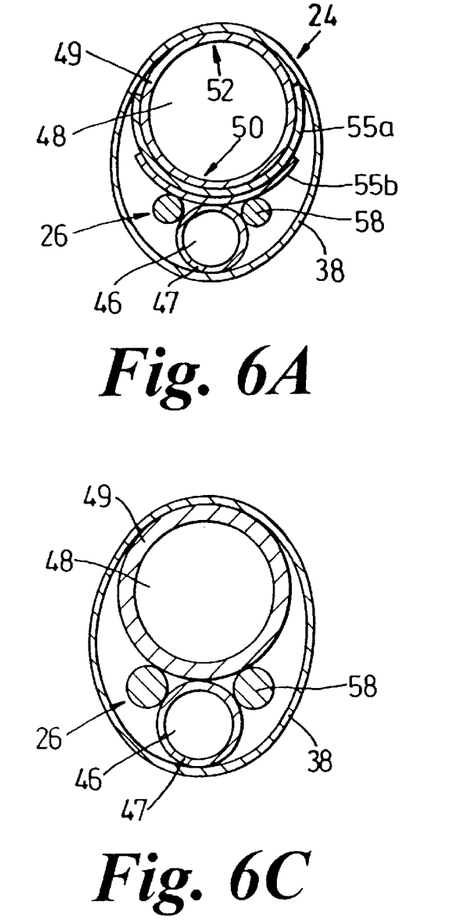
FIG. 6A is a cross-sectional view of a first embodiment of a catheter supporter taken on Line A—A in FIG. 2.
FIG. 6C is a cross-sectional view of the first embodiment of the catheter supporter taken on Line C—C in FIG. 2.
Figure 6B:
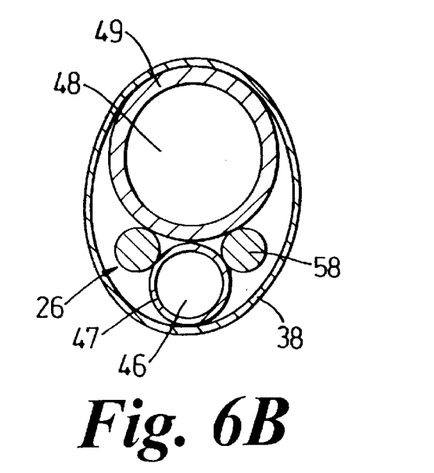
FIG. 6B is a cross-sectional view of the first embodiment of the catheter supporter taken on Line B—B in FIG. 2.

The catheter supporter 26 can be implemented in a number of alternate ways. For example, as shown in FIGS. 6A–C, the catheter supporter 26 can include a pair of spaced apart cylindrical shafts 58 positioned within the catheter outer structure 38 and extending substantially parallel with the guide wire lumen 46 and the delivery lumen 48. The cylindrical shafts 58 are widest proximate the catheter proximal end 40 and taper towards the delivery area 24.

Figure 7A:
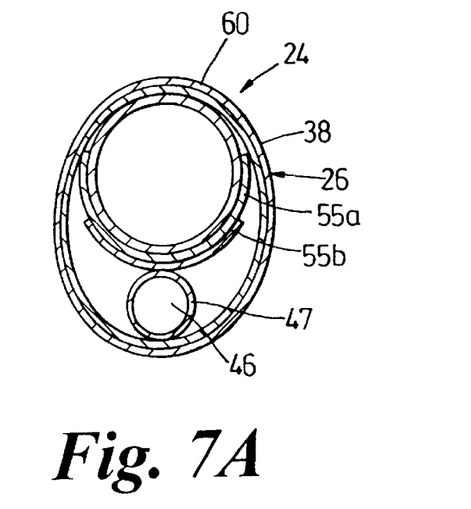
FIG. 7A is a cross-sectional view of a second embodiment of a catheter supporter taken on Line A—A in FIG. 2.
Figure 8:
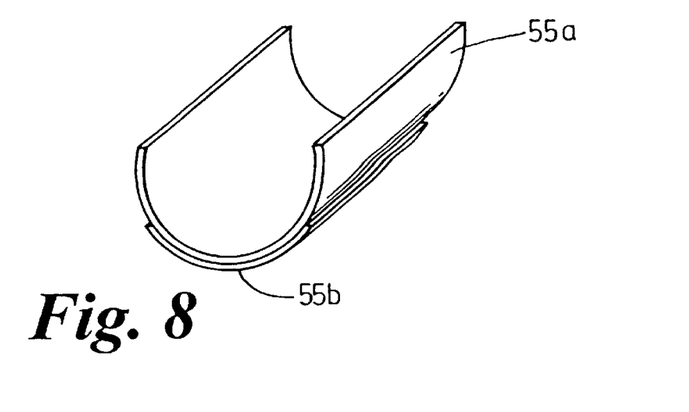
FIG. 8 is an enlarged, perspective view of a portion of an attenuator section having features of the present invention.

Alternately, as shown in FIG. 7A, the catheter supporter 26 can be a tubular member 60 which encompasses the guide wire lumen 46 and the delivery lumen 48. The tubular member 60 is positioned within the catheter outer structure 38 and is concentric with the outer structure 38. Similarly, the tubular member 60 is thickest proximate the catheter proximal end 40 and tapers towards the delivery area 24. Alternately, those skilled in the art would recognize other ways to design the catheter supporter 26.

The catheter supporter 26 must be sufficiently flexible to allow the catheter 22 to be positioned in small, curving vessels 14. The catheter supporter 26 can be made of a number of materials which include a composite of polymer and metallic components. For example, a suitable catheter supporter 26 can be made from the block copolymer sold under the trademark Pebax by Elf Atochem. The catheter supporter 26 provided herein also inhibits the guide wire lumen 46 and the delivery lumen 48 from collapsing.

The guide wire 28 is suitable for being inserted into the vessel lumen 36 and is used to guide the delivery area 24 through the vessel lumen 36 to the treatment site 12. A guide wire 28 having a diameter of about 0.014 inches is commonly used.

Referring to the FIG. 2, the radiation source 30 is sized to fit into the delivery lumen 48 and includes a delivery wire 62 and the radioactive area 32 attached to the delivery wire 62. The radiation source 30 inserts into the delivery area 24 and remains in the delivery area 24 until the proposed dosage is released. Thus, the amount of time that the radiation source 30 is positioned in the delivery area 24 depends upon the emittance of the radioactive area 32 and the proposed dosage requirements of the patient 16.

Preferably the radioactive area 32 emits β-rays since the β-rays have a relatively short tissue penetration level. Because of the short tissue penetration of β-rays, the medical staff is exposed to less radiation and the βrays can be controlled within the delivery area 24. Preferably, the radioactive area 32 also has a relatively high activity level so that the prescribed dose of radiation emits quickly into the patient 16. For example, for a radioactive area 32 which includes Rhenium could have an activity level of about 2 to 300 mCi and a usable tissue penetration level of between about 1.5 to 2.5 millimeters.

Typically, the radioactive area 32 is between about 0.5 to 10.0 centimeters in length and has a diameter of between approximately 0.1 millimeters to 2.0 millimeters. Additionally, the radioactive area 32 can be rechargeable and reusable to minimize radioactive waste.

Alternately, it is anticipated that the radioactive area 32 could include gamma emitters or a non-nuclear source could provide the radioactivity to the radioactive area 32.

Typically, the delivery device 10 is used in conjunction with a first imaging system 64 which provides an accurate and detailed map or image of the internal structure of the vessel 14. A suitable first imaging system 64 is an Intravascular Ultrasound System ("IVUS System") sold by Boston Scientific. The IVUS System uses ultrasonic waves to map or image the vessel 14. Referring to FIG. 2, the first imaging system 64 includes a first imaging catheter 66 which inserts directly into the vessel lumen 36 to image the structure of the vessel 14.

Further, the delivery device 10 can be used in conjunction with a second imaging system 68 which indicates when the delivery area 24 is properly oriented within the vessel lumen 36. An IVUS System also sold by Boston Scientific, can be used for the second imaging system 68. Referring to FIG. 2, the second imaging system 68 includes a second imaging catheter 70 which inserts into the delivery lumen 48 to determine when the delivery area 24 is properly oriented. If the second imaging system 68 is an IVUS System, the delivery lumen 48 must be filled with a substantially incompressible fluid (not shown), such as saline. It is anticipated that the same IVUS System can be used for the first imaging system 64 and the second imaging system 68.

Preferably, a sheath 72 can be used to protect or isolate the radiation source 30 from the incompressible fluid. Referring to FIG. 2, the sheath 72 is tubular cover which inserts into the delivery lumen 48. The sheath 72 provides a barrier and isolates the radiation source 30 from contact with the incompressible fluid. The sheath 72 can be made of a thin, high density polyethylene.

As shown in FIG. 2, the delivery device 10 can also include a dummy rod 74 for inserting the sheath 72 into the delivery lumen 48 and insuring that the delivery lumen 48 is not collapsed. The dummy rod 74 is designed to be substantially identical to the radiation source 30. Basically, the dummy rod 74 is used to install the sheath 72 and insure that the radioactive area 24 will move smoothly within the delivery lumen 48 to the delivery area 24.

OPERATION

An example of the operation of the delivery device 10 can best be visualized with initial reference to FIGS. 1 and 2. First, the guiding catheter is inserted into the coronary artery ostium. Next, the guide wire 28 is positioned into the vessel 14 of the patient 16. This is done to establish a mechanical pathway through the vessel 14. Subsequently, the first imaging catheter 66 of the first imaging system 64 is inserted into the vessel lumen 36, The first imaging system 64 provides an accurate and detailed map or image of the internal structure of the vessel 14. With the information obtained from the first imaging system 64, the location of the treatment site 12, the size and shape of the vessel wall 18, and the positioning of the vessel lumen 36 relative to the vessel lamina 34 can be determined.

Next, the first imaging catheter 66 is removed and an initial vascular procedure such as angioplasty, stenting, and/or atherectomy can optionally be performed upon the vessel 14. If an initial vascular procedure is performed on the vessel 14, the first imaging catheter 66 can be reinserted into the vessel lumen 36 to provide an accurate and detailed map or image of the residual internal structure of the vessel 14. The first imaging catheter 66 is then removed from the vessel lumen 36.

Importantly, the configuration of the vessel wall 18 and the vessel 14 can be determined with information from the first imaging catheter 66. Stated another way, the residual size and shape of the vessel wall 18 and the positioning of the vessel lumen 36 relative to the vessel lamina 34 can be determined. Based upon configuration of the vessel wall 18, the configuration of the attenuator section 50, i.e., the shape, size, and thickness of the attenuator section 50 can be selected to deliver the desired radiation dose profile.

Next, the guide wire lumen 46 of the catheter 22 is moved over the guide wire 28 until the delivery area 24 is adjacent to the treatment site 12. The markers 56 on the catheter 22, proximate the delivery area 24, allow the doctor to precisely determine the location the delivery area 24 using a fluoroscope.

With the delivery area 24 adjacent the treatment site 12, the second imaging catheter 70 and the incompressible fluid are inserted into the delivery lumen 48. The second imaging system 68 provides information about the shape of the vessel wall 18 through the window section 52. With this information, the catheter proximal end 42 is rotated until the second imaging system 68 indicates when the delivery area 24 is properly oriented, i.e., the window section 52 is adjacent where the vessel wall 18 is the thickest. Importantly, the catheter supporter 26 transmits torque smoothly and predictably between the catheter proximal end 42 and the catheter distal end 40. This allows for the precise orientation of the window section 52 adjacent the thickest area of the vessel wall 18 at the treatment site 12 and prevents collapse of the delivery lumen 48.

Subsequently, the catheter 22 is retained in this orientation and the second imaging catheter 70 is removed from the delivery lumen 48.

Next, the sheath 72 is installed with the dummy rod 74 into the delivery lumen 48. The dummy rod 74 is then removed and the sheath 72 remains in position within the delivery lumen 48 to protect the radiation source 30. The dummy rod 74 can be reinserted into and removed from the delivery lumen 48 a number of times to insure that the delivery lumen 48 is not collapsed and that the radioactive area 32 can be inserted into the delivery area 24 without delay.

Finally, the radioactive area 32 and the delivery wire 62 are inserted into the delivery lumen 48 until the radioactive area 32 is positioned within the delivery area 24. The radioactive area 32 remains positioned in the delivery area 32 and is allowed to emit radiation until the proposed dosage is released. Subsequently, the radiation source 30 is removed from the catheter 22 and stored in a safe container (not shown).

Importantly, the unique design of the delivery area 24, which includes the attenuator section 50, allows the delivery area 24 to emit an eccentric radiation dose profile so that the vessel lamina 34 receives a uniform dosage.

While the particular delivery device 10 as herein shown and disclosed in detail is fully capable of obtaining the objects and providing the advantages herein before stated, it is to be understood that it is merely illustrative of the presently preferred embodiments of the invention. For example, the present delivery device 10 is also capable of delivering a substantially uniform dose of radiation to other areas of the vessel 14, including the vessel adventitia 35. Thus, no limitations are intended to the details of the construction or design herein shown other than as defined in the appended claims.

What is claimed is:

1. A method for delivering radiation from a radiation source to a treatment site of a vessel, the vessel having a vessel lumen and a vessel lamina, the method comprising the steps of:

advancing a catheter into the vessel lumen, the catheter including a window section;

rotating an attenuator section inside the vessel lumen so that the attenuator section is closer than the window section to a point of vessel lamina which is closest to the radiation source when the radiation source is positioned within the catheter;

positioning the radiation source within the catheter; and attenuating a portion of the radiation emitting radially from the radiation source with the attenuator section which attenuates at least one percent of the radiation directed towards the attenuator section so that a radiation dose profile in the vessel relative to the radiation source is substantially asymmetrical.

2. The method of claim 1 wherein the step attenuating a portion of the radiation with an attenuator section includes attenuating with an attenuating material which includes gold.

3. The method of claim 1 including the step of determining the position of the attenuator section, relative to the vessel lamina, proximate to the treatment site.

4. The method of claim 1 comprising the step of inhibiting rotational deformation in the catheter with a catheter supporter which includes a metallic component for inhibiting rotational deformation.

5. A method for treating a treatment site of a vessel with radiation from a radiation source, the vessel having a vessel lumen and a vessel lamina, the method comprising the steps of:

positioning a delivery area of a catheter substantially adjacent the treatment site in the vessel lumen, the delivery area including an attenuator section and a window section, the attenuator section being adapted to attenuate more radiation than the window section;

rotating the delivery area until the attenuator section is closer than the window section to a point of the vessel lamina proximate the treatment site which is closest to the radiation source when the radiation source is positioned within the catheter; and positioning a radiation source within the catheter.

6. The method of claim 5, wherein the step of positioning the delivery area substantially adjacent the treatment site includes locating at least one marker which is secured to the catheter proximate the delivery area.

7. The method of claim 5 including the step of imaging the vessel to determine when the window section is substantially farthest away from the vessel lamina.

8. A delivery device adapted for positioning a radiation source proximate to a treatment site in a vessel, the vessel including a vessel wall, the delivery device comprising;

a catheter including a delivery area for receiving at least a portion of the radiation source, the catheter being adapted to at least partly be inserted in the vessel; and an attenuator section positioned proximate to the delivery area for attenuating the intensity of a portion of the radiation emitting radially from the radiation source, when a portion of the radiation source is positioned in the delivery area, the attenuator section including an attenuator material which includes gold.

9. The delivery device of claim 8 wherein the attenuator section attenuates a sufficient portion of the radiation emitting from the delivery area so that the delivery area emits a radiation dose profile which is substantially asymmetric relative to the radiation source.

10. The delivery device of claim 8 wherein the attenuator material has a density of at least approximately ten grams per cubic centimeter.

11. The delivery device of claim 8 including a catheter supporter secured to the catheter, the catheter supporter including a metallic component which substantially inhibits rotational deformation in the catheter between a catheter distal end and a catheter proximal end.

12. The delivery device of claim 8 wherein the catheter includes a guide wire, lumen a delivery lumen and a catheter supporter which comprises a tubular member which substantially encompasses the guide wire lumen and the delivery lumen to inhibit rotational deformation between a catheter distal end and a catheter proximal end.

13. A delivery device adapted for positioning a radiation source proximate to a treatment site in a vessel, the vessel including a vessel wall, the delivery device comprising:

a catheter including a delivery area for receiving at least a portion of the radiation source, the catheter being adapted to at least partly be inserted into the vessel; and an attenuator section positioned proximate to the delivery area for attenuating the intensity of a portion of the radiation emitting radially from the radiation source, when a portion of the radiation source is positioned in the delivery area, the attenuator section including an attenuator material which is a discrete element: wherein the catheter includes a guide wire lumen, a delivery lumen and a catheter supporter which comprises a substantially cylindrical shaft which extends substantially parallel with the guide wire lumen and the delivery lumen to inhibit rotational deformation between a catheter distal end and a catheter proximal end.

14. The delivery device of claim 8 comprising at least one marker positioned proximate the delivery area which can be used to indicate the position of the delivery area in the vessel.

15. The delivery device of claim 8 including at least one blocker which partly inhibits radiation from emitting longitudinally from the delivery area.

16. A delivery device adapted for positioning a radiation source proximate to a treatment site of a vessel, the delivery device comprising:

a catheter which is adapted to be at least partly inserted into the vessel, the catheter including a catheter distal end, a catheter proximal end, a delivery lumen and a delivery area for receiving a portion of the radiation source, the delivery area including an attenuator section and a window section; and a catheter supporter inhibiting rotational deformation of the catheter and allowing for rotation of the delivery area upon rotation of the catheter proximal end, the catheter supporter including a substantially cylindrical shaft which extends substantially parallel with the delivery lumen, the cylindrical shaft including a metallic component.

17. The delivery device of claim 16 wherein the catheter supporter extends from proximate the catheter proximal end to proximate the catheter distal end.

18. A method for treating a treatment site of a vessel with radiation from a radiation source, the vessel having a vessel lamina, the method comprising the steps of:

providing a delivery device including a delivery area for receiving the radiation source, the delivery area including an attenuator section and a window section;

positioning the delivery area substantially adjacent the treatment site in the vessel lumen; and imaging to determine the orientation of at least one of the attenuator section and the window section within the vessel.

19. The method of claim 18 including the step of rotating the delivery area until the attenuator section of the delivery device is substantially closest to the vessel lamina.

20. The method of claim 18 wherein the step of imaging includes the step of imaging through the window section of the delivery area.

* * * * *